(12) United States Patent
Crawford

(10) Patent No.: US 8,808,717 B2
(45) Date of Patent: Aug. 19, 2014

(54) CONTROL OF ECTOPARASITES

(75) Inventor: Michael J. Crawford, St. Louis, MO (US)

(73) Assignee: Bayer Animal Health GmbH, Leverkasen (DE)

(*) Notice: Subject to any disclaimer, the term of this patent is extended or adjusted under 35 U.S.C. 154(b) by 0 days.

(21) Appl. No.: 12/731,871

(22) Filed: Mar. 25, 2010

(65) Prior Publication Data

US 2010/0179206 A1 Jul. 15, 2010

Related U.S. Application Data

(63) Continuation of application No. 12/135,337, filed on Jun. 9, 2008.

(60) Provisional application No. 60/942,651, filed on Jun. 7, 2007.

(51) Int. Cl.
*A01N 25/34* (2006.01)
*A01N 25/02* (2006.01)
*A01N 43/36* (2006.01)

(52) U.S. Cl.
USPC ........... 424/405; 424/407; 424/409; 424/411; 514/403

(58) Field of Classification Search
None
See application file for complete search history.

(56) References Cited

U.S. PATENT DOCUMENTS

| | | | |
|---|---|---|---|
| 4,008,327 A | 2/1977 | Kathawala | |
| 4,631,231 A | 12/1986 | Stendel et al. | |
| 4,845,097 A | 7/1989 | Matsumoto et al. | |
| 4,950,668 A | 8/1990 | Okada et al. | |
| 5,039,693 A | 8/1991 | Okada et al. | |
| 5,124,333 A | 6/1992 | Obata et al. | |
| 5,217,523 A | 6/1993 | Ditrich et al. | |
| 5,296,484 A | 3/1994 | Coghlan et al. | |
| 5,411,963 A | 5/1995 | Dreikorn et al. | |
| 5,668,140 A | 9/1997 | Schaper et al. | |
| 5,703,064 A * | 12/1997 | Yokoi et al. | 514/80 |
| 6,335,363 B1 | 1/2002 | Gerlach et al. | |
| 6,387,933 B1 | 5/2002 | Nakamura et al. | |
| 7,025,289 B2 | 4/2006 | Hubmann et al. | |
| 7,205,289 B2 | 4/2007 | Fischer et al. | |
| 7,494,956 B2 | 2/2009 | Gauvry et al. | |
| 7,608,604 B2 | 10/2009 | Comlay et al. | |
| 2004/0106616 A1 | 6/2004 | Bakthavatchalam et al. | |
| 2007/0020304 A1 | 1/2007 | Tamarkin et al. | |
| 2007/0078172 A1 | 4/2007 | McElroy et al. | |
| 2007/0129407 A1 | 6/2007 | Koyanagi et al. | |
| 2010/0234219 A1* | 9/2010 | Lahm et al. | 504/100 |
| 2011/0183012 A1 | 7/2011 | Gewehr et al. | |

FOREIGN PATENT DOCUMENTS

| | | |
|---|---|---|
| GB | 2111830 | 7/1983 |
| JP | 2003089610 A | 3/2003 |
| JP | 2004067574 | 3/2004 |
| JP | 2006131516 | 5/2006 |
| JP | 2007045818 | 2/2007 |

OTHER PUBLICATIONS

Dekeyser, M., "Review: Acaricide mode of action" Pest Management Science 61:103-110, 2005.
Peter Lummen, "Mitochondrial Electron Transport Complexes as Biochemical Target Sites for insecticides and Acaricides" Complex I Acar. Insect. (2007), pp. 197-215.
Nobuyuki Nonaka, "Tolfenpyrad—A New Insecticide with Wide Spectrum and Unique Action", AJ (2003) No. 83:pp. 1-19.
Tolfenpyrad Technical Information (Nihon Nohyaku Co., Ltd.) May 8, 2001.
The Pesticide Manual, Tomlin C.D.S. XIII, Ed. 2003 pp. 862.
White, W.H., et al., "An in Vitro Larval Immersion Microassay for Identifying and Characterizing Candidate Acaricides," 2004, J Med Entomol, pp. 1034-1042.

* cited by examiner

*Primary Examiner* — Neil Levy

(57) ABSTRACT

Disclosed is a method of controlling ectoparasites that infest companion and livestock animals by applying to the animal an effective amount of 4-tert-butylphenethyl quinazolin-4-yl ether or 4-chloro-5-ethyl-2-methyl-N-[(4-tert-butylphenyl)methyl]pyrazole-3-carboxamide or 5-chloro-N-[2-[4-(2-ethoxyethyl)-2,3-dimethylphenoxy]ethyl]-6-ethyl-4-pyrimidinamine or 4-chloro-3-ethyl-1-methyl-N-[4-(p-tolyloxy)benzyl]pyrazole-5-carboxamide.

8 Claims, No Drawings

CONTROL OF ECTOPARASITES

This application is a continuation of U.S. Ser. No. 12/135,337, filed Jun. 9, 2008, which in turn claims priority from U.S. Ser. No. 60/942,651, filed Jun. 7, 2007. The entirety of both applications is hereby incorporated by reference.

BACKGROUND

In the rearing of animals, such as companion animals and livestock, ectoparasites cause enormous losses, including economic losses, particularly because many ectoparasites can act as disease vectors.

The control of animal ectoparasites is an ongoing challenge. For example, numerous strains of ticks have developed resistance to a wide range of pesticides such as arsenic, hexachlorohexane, camphechlor, DDT, pyrethrines, carbamates and organophosphorous compounds despite the fact that these compounds have varied modes of action and several distinct primary sites of attack in the ectoparasite. It is therefore generally accepted that it is highly desirable to develop and commercialize additional active agents with new modes of action for ectoparasite control.

Compounds harboring a quinazoline, pyrazole or pyrimidine core are well known for their fungicidal, insecticidal and miticidal use in the crop chemistry applications (e.g., U.S. Pat. No. 5,411,963). However several reports have indicated that fenazaquin and tebufenpyrad have limited spectrum of activity against insect pests as well as relatively low toxicity to beneficial mite species under normal use (*Pest Manag Sci* 2005 61(2):103-10).

SUMMARY

Described herein are methods for preventing and/or repressing ectoparasites of animals. The methods include the application to the animal of an effective amount of a composition that includes one or more of: 4-tert-butylphenethyl quinazolin-4-yl ether (fenazaquin), 4-chloro-5-ethyl-2-methyl-N-[(4-tert-butylphenyl)methyl]pyrazole-3-carboxamide (tebufenpyrad), 5-chloro-N-[2-[4-(2-ethoxyethyl)-2,3-dimethylphenoxy]ethyl]-6-ethyl-4-pyrimidinamine (pyrimidifen), and 4-chloro-3-ethyl-1-methyl-N-[4-(p-tolyloxy)benzyl]pyrazole-5-carboxamide (tolfenpyrad). Fenazaquin, tebufenpyrad, pyrimidifen, and tolfenpyrad are thought to affect metabolism by inhibiting the mitochondrial electron transport chain by binding with Complex I at co-enzyme $Q_0$ and represent a novel mode of action for ectoparasite control in animal health.

The unexpected anti-tick and anti-flea properties of certain mitochondrial electron transport inhibitors are of considerable significance since there are relatively few agricultural pesticides that can be effectively be used against ectoparasites of animals.

Compositions and processes for controlling ectoparasites of animals are described herein. The methods entail the use of compositions that include: 4-tert-butylphenethyl quinazolin-4-yl ether (Formula I), 4-chloro-5-ethyl-2-methyl-N-[(4-tert-butylphenyl)methyl]pyrazole-3-carboxamide (Formula II), 5-chloro-N-[2-[4-(2-ethoxyethyl)-2,3-dimethylphenoxy]ethyl]-6-ethyl-4-pyrimidinamine (Formula III) and 4-chloro-3-ethyl-1-methyl-N-[4-(p-tolyloxy)benzyl]pyrazole-5-carboxamide (Formula IV), to control ticks, mites, fleas, flies, and lice that infest animals.

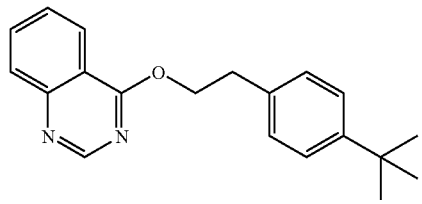

Formula I

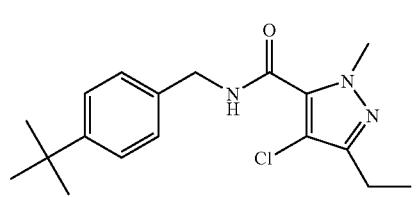

Formula II

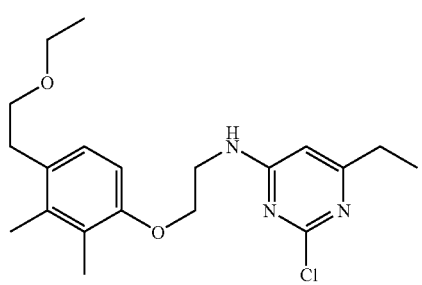

Formula III

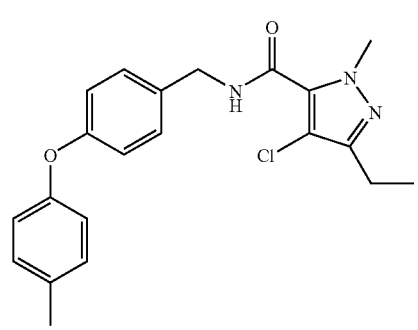

Formula IV

The compounds in Formula I, Formula II, Formula III and Formula IV are suitable for controlling arthropods which attack agricultural livestock such as, for example, cattle, sheep, goats, horses, pigs, donkeys, camels, buffaloes, rabbits, chickens, turkeys, ducks, geese, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, and the like) can be lessened, so that more economical and simpler animal husbandry is possible.

Described herein is a method for treating non-human subject, the method comprising administering to the subject a composition comprising the compound of Formula I or a salt thereof.

Described herein is a method for treating non-human subject, the method comprising administering to the subject a composition comprising the compound of Formula II or a salt thereof.

Described herein is method for treating non-human subject, the method comprising administering to the subject a composition comprising the compound of Formula III or a salt thereof.

Described herein is a method for treating non-human subject, the method comprising administering to the subject a composition comprising the compound of Formula II or a salt thereof.

In various embodiments of the methods described herein: the non-human subject is a mammal; the non-human subject is a bird; the administration comprises topical administration, the administration comprises parenteral (e.g., oral) administration; and the non-human subject is infested with an ectoparasite or is at risk of infestation with an ectoparasite. In various embodiments: the ectoparasite is an arthropod; ectoparasite is selected from the families Ixodidae, Argasidae, Psoroptidae, Sarcoptidae, Muscidae, Trichodectidae or Pulicidae; the ectoparasite is selected from *Boophilus* spp, *Rhipicephalus* spp, *Dermacentor* spp, *Hyalomma* spp, *Amblyomma* spp, *Otobius* spp, *Ornithodoros* spp, *Damalinia* spp, *Stomoxys* spp, *Bovicola* spp or *Ctenocephalides* spp.

In various embodiments of the methods described herein: the composition is a solid; the composition is a liquid or gel; the administration comprising applying a liquid composition comprising the compound to the non-human subject; the administration comprising applying a solid composition comprising the compound to the non-human subject; the administration comprises spraying, dipping, or spotting the onto the non-human subject; the compound is present in the liquid composition at 0.01 to 50.0% by weight; the compound is present in the liquid composition at 0.02 to 10.0% by weight; the non-human subject is selected from: cattle, sheep, goats, pigs, dogs, cats and horses; the topical administration comprises fitting the non-human subject with a solid article comprising the composition (e.g., a tag, a collar, a collar tag, an ear tag, a tail tag, a limb band or a halter); the solid article comprises a polymeric material.

Described herein is a pharmaceutical composition comprising the compound of Formula I or a salt thereof in a unit dosage form.

Described herein is a pharmaceutical composition comprising the compound of Formula II or a salt thereof in a unit dosage form.

Described herein is a pharmaceutical composition comprising the compound of Formula III or a salt thereof in a unit dosage form.

Described herein is a pharmaceutical composition comprising the compound of Formula IV or a salt thereof in a unit dosage form.

Described herein is a composition comprising the compound of Formula I or a salt thereof, wherein the composition is suitable for topical administration to a non-human subject.

Described herein is a composition comprising the compound of Formula I or a salt thereof, wherein the composition is suitable for topical administration to a non-human subject.

Described herein is a composition comprising the compound of Formula II or a salt thereof, wherein the composition is suitable for topical administration to a non-human subject.

Described herein is a composition comprising the compound of Formula III or a salt thereof, wherein the composition is suitable for topical administration to a non-human subject.

Described herein is a composition comprising the compound of Formula IV or a salt thereof, wherein the composition is suitable for topical administration to a non-human subject.

In various embodiment the composition is a powder.

The details of one or more embodiments of the invention are set forth in the accompanying description below. Other features, objects, and advantages of the invention will be apparent from the description and from the claims.

DETAILED DESCRIPTION

Several compounds having activity as mitochondrial complex I inhibitors were commercialized in the 1990s for the purpose of protecting crops and other plants from predation by plant pests such as spider mites (e.g., two spotted spider mite) or rust mites (e.g., apple rust mite). These compounds include fenazaquin (4-tert-butylphenethyl quinazolin-4-yl ether; Formula I), tebufenpyrad (4-chloro-5-ethyl-2-methyl-N-[(4-tert-butylphenyl)methyl]pyrazole-3-carboxamide; Formula II), pyrimidifen (5-chloro-N-[2-[4-(2-ethoxyethyl)-2,3-dimethylphenoxy]ethyl]-6-ethyl-4-pyrimidinamine), tolfenpyrad (4-chloro-3-ethyl-1-methyl-N-[4-(p-tolyloxy) benzyl]pyrazole-5-carboxamide; Formula IV), fenpyroximate (tert-butyl 4-[[(1,3-dimethyl-5-phenoxy-pyrazol-4-yl) methylideneamino]oxymethyl]benzoate) and pyridaben (4-chloro-2-tert-butyl-5-[(4-tert-butylphenyl)methylsulfanyl]pyridazin-3-one).

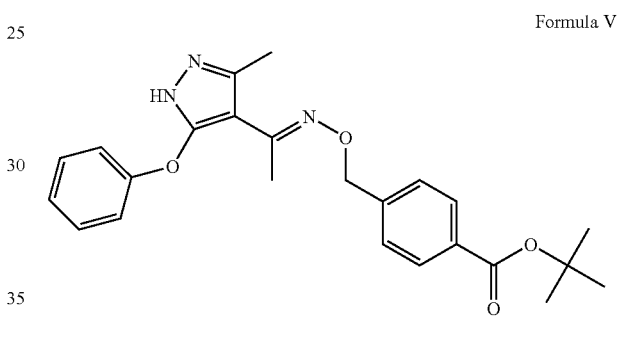

(fenpyroximate)

Formula V

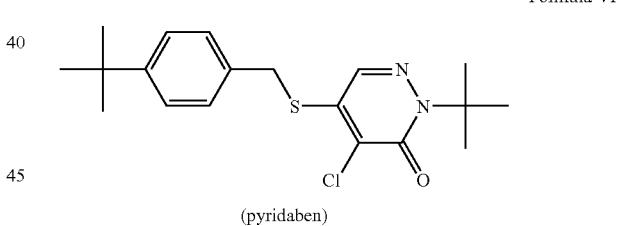

(pyridaben)

Formula VI

Despite acting at a conserved site (coenzyme $Q_o$ of Complex I) and interfering with an essential process (mitochondrial electron transport) these pesticides nonetheless show surprising and unpredictable species selectivity. Although used primarily as acaricides against plant parasitic mites, these compounds generally demonstrate minimal impact on predatory mites and many beneficial insects under field conditions (*Pest Manag Sci* 2005 61(2):103-10).

A specific example of the large species dependent differences in potency of complex I inhibitors is seen for fenazaquin in a study by Hackler et al. Fenazaquin is highly active against cotton aphids ($LC_{50}$ of 2.6 ppm) and against mosquito larvae ($LC_{50}$ of 0.725 ppm) but has low potency against the cabbage looper ($LC_{50}$ 188 ppm) and greater than 400 ppm activity against both southern corn rootworm and tobacco budworm (Hackler et al. 1998 Development of broad-spectrum insecticide activity from a miticide. In: *Synthesis and Chemistry of Agrochemicals V* (Baker et al., eds), American Chemical Society, Washington D.C., pp. 147-156). These species sensitivity differences could be due to intrinsic activity differences (i.e., active site changes), metabolism differences and/or penetration differences. For example, fenazaquin is extensively metabolized by the tobacco bud worm, which may explain the poor efficacy against this species. Additionally fenazaquin is degraded more extensively by rat liver microsomes than by trout liver microsomes which may partially explain the higher toxicity of the compound to fish than to mammals. At present, these species-dependent differences in the interactions of the compounds with the active sites, or metabolism or penetration differences are impossible to predict a priori.

Surprisingly we have found that fenazaquin (4-tert-butylphenethyl quinazolin-4-yl ether) and certain other mitochondrial complex I inhibitors are active on fleas and ticks, two distantly related groups of arthropods that are both commercially important ectoparasites in animal husbandry.

The compounds 4-tert-butylphenethyl quinazolin-4-yl ether, 4-chloro-5-ethyl-2-methyl-N-[(4-tert-butylphenyl)methyl]pyrazole-3-carboxamide, 5-chloro-N-[2-[4-(2-ethoxyethyl)-2,3-dimethylphenoxy]ethyl]-6-ethyl-4-pyrimidinamine, and 4-chloro-3-ethyl-1-methyl-N-[4-(p-tolyloxy)benzyl]pyrazole-5-carboxamide are contemplated to be active against animal parasites (ectoparasites) such as hard ticks, soft ticks, mange mites, harvest mites, lice, hair lice, bird lice and fleas. These parasites include the ectoparasites of the order Acari of the family Ixodidae, e.g., the cattle ticks such as *Boophilus* spp, e.g, *Boophilus microplus, Boophilus decoloratus* and *Boophilus annulatus; Rhipicephalus* spp such as *Rhipicephalus sanguineus, Rhipicephalus appendiculatus, Rhipicephalus pulchellus* and *Rhipicephalus evertsi; Hyalomma* spp such as *Hyalomma truncatum, Hyalomma rufipes, Hyalomma detritum, Hyalomma marginatum, Hyalomma dromedarii* and *Hyalomma anatolicum excavatum; Dermacentor* species such as *Dermacentor variabilis* and *Dermacentor andersoni; Amblyomma* spp such as *Amblyomma variegatum, Amblyomma herbraeum, Amblyomma pomposum, Amblyomma americanum, Amblyomma cayennense, Amblyomma maculatum, Amblyomma gemma* and *Amblyomma lepidium*; of the family Argasidae, e.g., *Otobius* spp such as *Otobius megnini* and *Ornithodoros* spp such as *Ornithodoros savignyi, Ornithodoros lahorensis* and *Ornithodoros tholozani*; of the family Psoroptidae, e.g., *Psoroptes ovis* and *Psoroptes equi*; and of the family Sarcoptidae e.g. *Sarcoptes bovis* or *Sarcoptes scabici*; ectoparasites of the order Diptera, which includes biting and sucking flies; ectoparasites of the order Phthiraptera, which includes sucking and chewing lice; and ectoparasites of the order Siphonaptera, including but not limited to the cat flea (*Ctenocephalides felis*) and the dog flea (*Ctenocephalides canis*).

The active compounds can be enterally administered in the form of, for example, tablets, capsules, potions, drenches, granules, pastes, boluses, the feed-through method, suppositories. The compounds can be parenterally administered such as, for example, by injections (intramuscularly, subcutaneously, intravenously, intraperitoneally and the like). The compounds can also be administered as implants, by nasal administration, by dermal administration in the form of, for example, immersing or dipping, spraying, pouring-on, spotting-on, washing, dusting, and with the aid of active-compound-comprising molded articles such as collars, ear tags, tail tags, limb bands, halters, marking devices and the like.

The active compound content of the use forms prepared from the commercially available formulations can vary within wide limits. The active compound concentration of the use forms can be from 0.0000001 to 95% by weight of active compound, preferably between 0.0001 and 10% by weight.

When used for cattle, poultry, domestic animals and the like, the active compound combinations can be applied as formulations (for example powders, emulsions, flowables) comprising the active compounds in an amount of 1 to 80% by weight, either directly or after 100- to 10,000-fold dilution, or they may be used as a chemical dip.

The compounds of formula I, II, III and IV are applied to the ectoparasites of the order Acari, in free base form or in agriculturally acceptable acid addition salt form, e.g., as hydrochloride or acetate, by topical treatment of the animals, e.g., by dusting, by dipping or by spray treatments with dilute aqueous form. The compounds of formula I, II, III and IV are preferably used in free base form. The degree of dilution may vary although preferably a concentration in the range of 0.01 to 50.0%, particularly of 0.02 to 10%, by weight of the active agent is employed. The treatment is preferably repeated at intervals of between 7 to 21 days.

The active agent can be conveniently formulated as a dust, dust concentrate, wettable powder, emulsifiable concentrate or as a solution, with conventional solid or liquid adjuvants. Particularly preferred compositions of the invention are liquid concentrates, especially those containing preferably 3.0 to 50% by weight of active agent, to be diluted with water before use. Such liquid concentrate preferably includes an emulsifying agent such as a polyglycolether derived from a high molecular weight alcohol, mercaptan or alkyl phenol with an alkylene oxide as well as a diluent such as a liquid aromatic hydrocarbon or mineral oil.

Suitable solid carriers are for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils. It is possible to use colorants such as inorganic pigments, for example iron oxide, titanium oxide and Prussian Blue, and organic colorants such alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The action of the compounds in Formula I, II, III and IV against animal ectoparasites can be seen from the examples which follow. The examples are to be construed as merely illustrative, and not limitative of the remainder of the disclosure in any way whatsoever. All of the publications cited herein are hereby incorporated by reference in their entirety.

EXAMPLE 1

Activity Against *A. Americanum* Larvae in a Dip Survival Assay

Using a previously-described protocol that can effectively predict compound potency against adult ticks in the field (White, W H. et al., An in vitro larval immersion microassay for identifying and characterizing candidate acaricides. J Med Entomol. 2004 November; 41(6):1034-42), test compounds from a dimethyl sulfoxide (DMSO) stock or 2% DMSO alone were dispensed into a round-bottom 96-well plate and mixed with aqueous buffer containing 1% ethanol and 0.2% Triton X100. The final DMSO concentration does not exceed 2%. Larval-stage lone star ticks (*Amblyomma americanum*) were dispensed into the wells containing test compounds and submerged for 30 minutes. The ticks were subsequently dispensed into a tissue biopsy bag, which is allowed to dry for 1 hour. After drying, the bags were incubated at 25° with 95% humidity for 24 hours and the number of live and dead larvae were counted. The results of this study are presented in Table 1.

TABLE 1

Number of live/total tick larvae
24 hours after treatment

| Treatment: | Concentration | | |
|---|---|---|---|
| DMSO | 2% 43/45 | | |
| Formula I | 0.05% 0/48 | 0.01% 0/51 | 0.001% 23/80 |
| Formula II | 0.05% 0/69 | 0.01% 0/77 | 0.001% 38/85 |
| Formula III | 0.05% 0/55 | 0.01% 0/62 | 0.001% 24/57 |
| Formula IV | 0.05% 0/76 | 0.01% 0/79 | 0.001% 58/114 |

EXAMPLE 2

Activity Against *C. Felis* Ova

Evaluation of test compounds against flea ova is a commonly-used assay for the determination of commercial efficacy against these insect parasites (McTier T L et al., Evaluation of the effects of selamectin against adult and immature stages of fleas (*Ctenocephalides felis felis*) on dogs and cats. Vet Parasitol. 2000 Aug. 23; 91(3-4):201-12; Dryden M et al., Efficacy of a topically applied formulation of metaflumizone on cats against the adult cat flea, flea egg production and hatch, and adult flea emergence. Vet Parasitol. 2007 Dec. 15; 150(3):263-7). Compounds were dissolved in acetone and 100 μl of each solution was placed in 5 ml glass vials and allowed to air dry. Forty ova from cat flea (*Ctenocephalides felis*) that were less than 48 hours old as well as flea dirt (primarily adult flea fecal material and host dander) were placed in the vials. Vials were covered with paper towels to allow air exchange and incubated at 25° with 90% humidity for 5 days, and the number of larvae were counted. The results of this study are presented in Table 2:

TABLE 2

Number of flea larvae emerging
(percent of total eggs) from 40 ova after 5 days.

| Treatment: | Amount per vial | | |
|---|---|---|---|
| Acetone | | 8 (20%) | |
| Formula I | 1 mg 1 (2.5%) | 100 μg 1 (2.5%) | 10 μg 4 (10%) |
| Formula II | 1 mg 1 (2.5%) | 100 μg 1 (2.5%) | 10 μg 7 (17.5%) |
| Formula III | 1 mg 1 (2.5%) | 100 μg 0 (0%) | 10 μg 1 (2.5%) |
| Formula IV | 1 mg 0 (0%) | 100 μg 0 (0%) | 10 μg 6 (15%) |

What is claimed:

1. A method for treating a non-human mammal infested with an ectoparasite, the method comprising topically administrating to the non-human mammal an effective amount of a composition consisting of 4-chloro-3-ethyl-1-methyl-N-[4-(p-tolyloxy)benzyl]pyrazole-5-carboxamide or a salt thereof, wherein the ectoparasite is selected from the group consisting of ticks, lice, flies and fleas, selecting from *Boophilus* spp. *Rhipicephalus* spp, *Dermacentor* spp, *Hyalomma* spp, *Amblyomma* spp, *Otoblus* spp, *Ornithodoros* spp, *Damalinia* spp, *Bovicola* spp, the order Diptera or *Ctenocephalides* spp, and wherein the non-human mammal is selected from the group consisting of livestock and domestic mammals.

2. A method claim according to claim 1 wherein the composition is a solid.

3. A method claim according to claim 1 wherein the composition is a liquid or gel.

4. A method according to claim 1 wherein the administration comprises spraying, dipping, or spotting the composition onto the non-human mammal.

5. A method according to claim 1 wherein the non-human mammal is selected from: cattle, sheep, goats, pigs, dogs, cats and horses.

6. A method according to claim 1 wherein the topical administration comprises fitting the non-human mammal with a solid article comprising the composition.

7. A method according to claim 6 wherein the solid article is selected from: a collar, a collar tag, an ear tag, a limb band or a halter.

8. A method according to claim 7 wherein the solid article comprises a polymeric material.

* * * * *